(12) United States Patent
Fischer et al.

(10) Patent No.: US 8,082,924 B2
(45) Date of Patent: Dec. 27, 2011

(54) IMMOBILIZING DEVICE FOR A PART OF A BODY

(75) Inventors: Patrizia Fischer, Oberwill-Lieli (CH); Thomas Müller, Wädenswil (CH); Ralph Müller, Herrliberg (CH)

(73) Assignee: ETH Zuerich, Zurich (CH)

( * ) Notice: Subject to any disclaimer, the term of this patent is extended or adjusted under 35 U.S.C. 154(b) by 251 days.

(21) Appl. No.: 12/518,894

(22) PCT Filed: Jan. 2, 2008

(86) PCT No.: PCT/EP2008/000001
§ 371 (c)(1),
(2), (4) Date: Jun. 12, 2009

(87) PCT Pub. No.: WO2008/086943
PCT Pub. Date: Jul. 24, 2008

(65) Prior Publication Data
US 2010/0078034 A1      Apr. 1, 2010

(30) Foreign Application Priority Data

Jan. 17, 2007    (EP) ...................................... 07000937

(51) Int. Cl.
*A61B 19/00*      (2006.01)
(52) U.S. Cl. ............................................ 128/869; 602/6
(58) Field of Classification Search .................... 128/869
See application file for complete search history.

(56) References Cited

U.S. PATENT DOCUMENTS

| | | | | |
|---|---|---|---|---|
| 2,800,129 A | * | 7/1957 | Van Swaay | ........................ 602/7 |
| 3,701,349 A | * | 10/1972 | Larson | ............................. 602/14 |
| 3,745,998 A | * | 7/1973 | Rose | ................................... 602/6 |
| 4,657,003 A | | 4/1987 | Wirtz | |
| 5,009,318 A | | 4/1991 | Lepinoy | |
| 5,865,166 A | * | 2/1999 | Fitzpatrick et al. | ........ 128/117.1 |
| 5,954,676 A | | 9/1999 | Kramer, III | |
| 6,882,878 B2 | | 4/2005 | Schmit et al. | |
| 2003/0176825 A1 | * | 9/2003 | Yavnai | ............................. 602/13 |
| 2005/0001109 A1 | * | 1/2005 | Walsh et al. | ................. 248/74.3 |
| 2005/0222529 A1 | | 10/2005 | Cuypers et al. | |

FOREIGN PATENT DOCUMENTS

| | | |
|---|---|---|
| DE | 3538887 A1 | 5/1986 |
| DE | 4423755 A1 | 1/1995 |
| EP | 0355930 A2 | 2/1990 |
| EP | 1582187 A1 | 10/2005 |
| GB | 1531268 A | 11/1978 |
| WO | 2006110028 A1 | 10/2006 |

* cited by examiner

*Primary Examiner* — Patricia Bianco
*Assistant Examiner* — Raymond E Harris
(74) *Attorney, Agent, or Firm* — Laurence A. Greenberg; Werner H. Stemer; Ralph E. Locher

(57) ABSTRACT

An immobilizing device for immobilizing a body part includes a bag which is filled with a granular material and is placed over the body part, an outer shell in which the bag is mounted and a hollow space formed between the outer shell and the bag for receiving pressured air in order to produce a force on the bag for immobilizing the body part. The device provides combined advantages over conventional devices, such as almost no absorption of x-rays, a perfect fit for every kind of body part, comfort for a patient, reusability, low cost, neutral smell, very light weight and easy application.

7 Claims, 2 Drawing Sheets

IMMOBILIZING DEVICE FOR A PART OF A BODY

This invention relates to an immobilizing device for a part of a body. The device includes an outer shell, a bag which is to be placed over the body part and is mounted in the outer shell and a granular material filling the bag.

BACKGROUND OF THE INVENTION

Field of the Invention

Immobilizing devices are frequently used for stabilizing and positioning a part of a body during a medical analysis such as computed tomography CT, high-resolution CT or magnetic resonance imaging MRI. In vivo CT scanning involves the use of X-rays being passed through a body or through a part of a body to produce cross sectional images of body tissue. MRI involves the use of electromagnets and short bursts of powerful magnetic fields and radio waves. For the aforementioned analysis it is a key issue, to have absolutely no motion in the area of the body being imaged. Patient motion is an ever-present-problem. During a measurement with one of the above mentioned devices the patient must remain absolutely still. If this requirement is not fulfilled, the resulting images are not interpretable. This is known as <<motion artefact>>. Especially in MRI a measurement may last up to 20 minutes, where CT has shorter durations but higher requirements for the stillness of a part of the body to be examined.

In order to immobilize a body or a part of a body the following cited documents revealed appropriate devices:

The document U.S. Pat. No. 5,009,318[1] discloses an apparatus for cushioning and maintaining an object by a device having a quantity of granular material. The apparatus comprises a retaining element defining a plurality of closed chambers, each chamber enclosing a portion of the granular material. Furthermore a sealed housing made of material impermeable to gas encloses the retaining element. By depressurization of the inner volume of the sealed housing a part of a body is being immobilized.

The paper EP 1 582 187 B1 [2] describes a hybrid immobilisation device comprising two parts, each of them made of thermoplastic material with different melting temperatures. The first part is shaped by heating in order to soften it so it becomes mouldable on the patients' body. The second part has the function of fixing the position of the first part with respect to the patients' body. The higher melting point of the material of the second part avoids deforming the second part while melting and moulding the first part with the lower melting point.

In U.S. Pat. No. 4,657,003[5] an immobilizer device with the principle of a vacuum mattress is disclosed.

The above mentioned devices suffer from the drawback either of a relatively complicate handling like
  a vacuum has to be provided or
  the parts have to be heated or
  the immobilization quality is not sufficient.

The immobilization device for a lower leg according to WO 2006/110028 A1 [4] has a pumping chamber and a flexible chamber with a fluid connection between the said chambers. During walking when the foot is lifted a fluid flows partly from the flexible chamber to the pumping chamber in order to apply a varying pressure to the lower leg. Obviously this device is only useable for legs.

The apparatus disclosed in U.S. Pat. No. 6,882,878 B2 [3] is considered to be the closest prior art to the present invention. This apparatus comprises a castable sleeve including a proximal layer and a distal layer, the proximal layer contacting a portion of a patients' limb and an expandable sleeve surrounding the distal layer of the castable sleeve, wherein the two layers form an inner space. The inner space receives a quick cast material to be optimally dispersed throughout the castable sleeve. The resulting force on the proximal layer immobilizes the portion of a patients' limb. This apparatus has the drawback that for each individual patient a part of the device has to be fabricated. Apart from being cost intensive, it requires time and chances that a patient even needs more than one device (pre- and postoperative examinations) is present.

BRIEF SUMMARY OF THE INVENTION

The object of the present invention is to overcome the problems presented by the above cited devices. There is a need for a device, which fulfils the following quoted requirements:
  fixation, so that the patient is incapable of moving his part of a body, e.g. a forearm, more than 50 μm, therefore improved image quality by decreased motion artefacts;
  influence on the quality of the image as low as possible;
  easy to handle;
  fits everyone (even patients with rheumatism);
  no pain and comfortable for the patient;
  reusability for both cast and filling material.

This object is solved by an immobilizing device for immobilizing a body part. The device includes an outer shell, a bag which is to be placed over the body part and is mounted in the outer shell and a granular material filling the bag. The outer shell and the bag form a hollow space therebetween for receiving pressured air to produce a force on the bag for immobilizing the body part.

The immobilizing device has the positive properties:
  almost no absorption of X-rays;
  perfect fit for every kind of a part of a body;
  comfortable for a patient;
  reusable;
  cheap;
  neutral smell;
  very light.

BRIEF DESCRIPTION OF THE SEVERAL VIEWS OF THE DRAWING

The invention will be now described in a preferred embodiment with reference to the accompanying drawings wherein.

DESCRIPTION OF THE INVENTION

Figure 1:
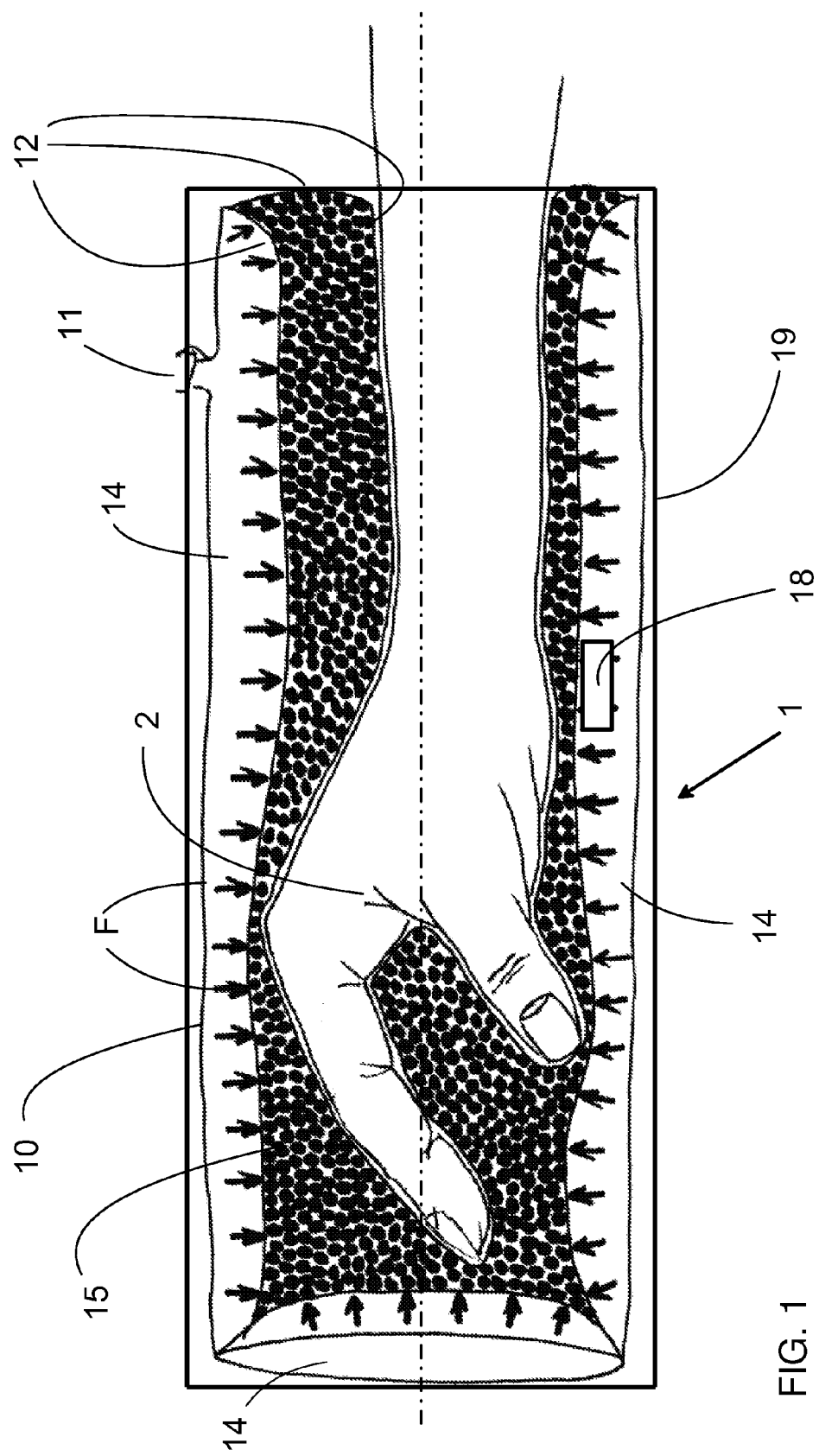
FIG. 1 is a view of an immobilizing device.

The principle of an immobilizing device according to the present invention is depicted in figure with the elements: A bag 12 filled with a granular material, which can be pearls 15, is put over a part of a body 2, in FIG. 1 that part of a body 2 is a forearm. The reference sign 12 in FIG. 1 denotes also the layers of the bag 12. The bag 12 is mounted into an outer shell 10. Between the outer shell 10 and the bag 12 there is a hollow space 14 for receiving pressured air in order to produce a force F on the bag 12. This force F acts on the granular material 15 which itself acts on the part of the body for an immobilizing or fixing in a defined position of said part of a body.

Figure 3:
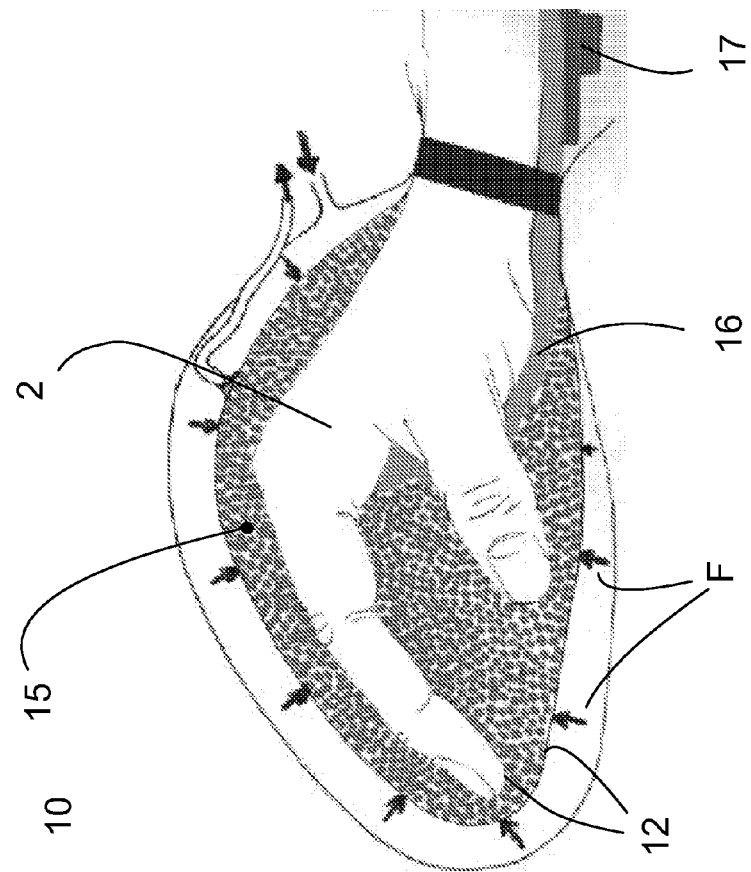
FIG. 3 application of an immobilizing device.
Figure 2:
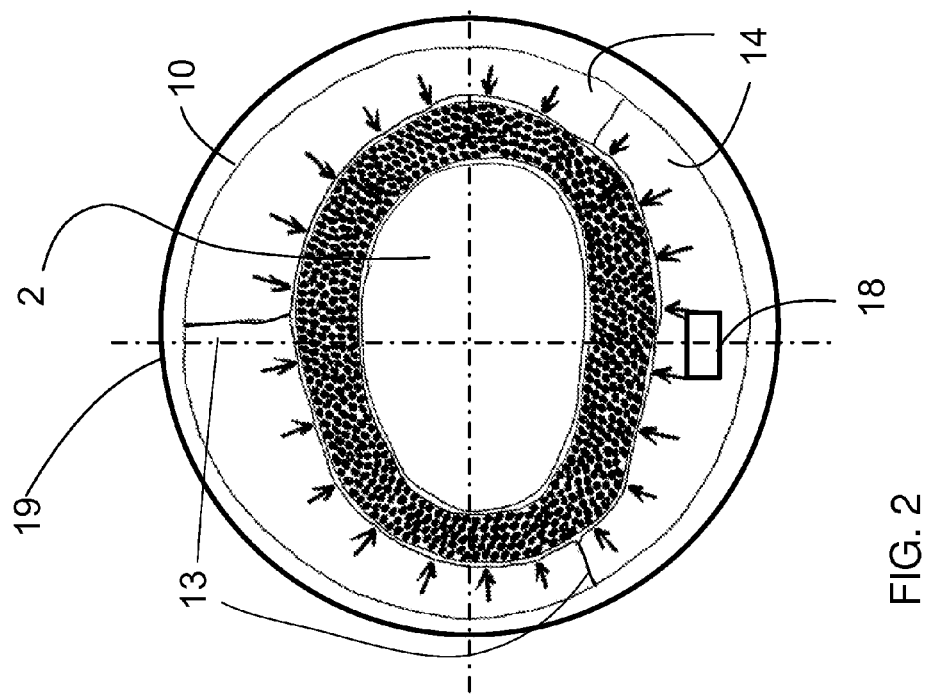
FIG. 2 cross sectional view of the immobilizing device.

One application of the immobilizing device 1 is as follows and partly depicted in FIG. 3:

To ensure a correct position of the patient's part of a body 2, a small cast 16 made out of composite or thermoplastic material is produced for each patient. An example of such an impression material is OPTOSIL ™. A bar 17 is inserted in the cast to provide a connection to the outer shell 10. The patient puts his hand together with this cast into the bag 12 with two layers, which is then tightened behind the region to be measured with a strap including an adjustable fastener, such as VELCRO™. At this stage, the two bags are close together and the inner one is filled with pearls made of polystyrene. The patient's hand is therefore surrounded by hundreds of tiny balls or pearls 15. The cast 16 now gets connected with the tube; the tube is not shown in FIGS. 1 and 3. Then a pump will be connected to the valve and air is pumped into the empty space between the two layers of the bag 12. As the outer one is absolutely inelastic because of the tube, the only way for the air to expand is to push the inner skin closer to the patient's hand. As a result the pearls 15 between the inner skin and the patient's hand get compressed and apply a pressure onto the hand, so that a movement of the hand is no longer possible.

Further advantageous embodiments of the invention may comprise:

The outer shell 10 is surrounded by a cylinder of inelastic material, e.g. a cylinder made of a transparent thermoplastic, such as, PLEXIGLAS ™ or another inelastic material, not shown in the figures.

Sensor for measuring the pressure; a signal representing the pressure derived from that sensor is transferred to a controlling device in order to maintain a pressure enabling a fixed position of the part of the body 2, e.g blood pressure control.

The hollow space between the outer shell 10 and the bag 12 can be separated in chambers 14, each chamber is separated from an other chamber by a wall 13.

A possible drawback may be the reproducibility of the measurement region for follow up measurements. This drawback can be solved using additional body positioning devices 16, 17 out of composite or thermoplastic material as described above. This ensures the reproducible positioning over several longitudinal measurements.

Depending on the examination method as e.g. CT or MRI the materials used for the immobilization device 1 may be chosen as follows:

For Computed Tomography CT

In principal every material can be scanned by a CT. Nevertheless metallic parts or high density materials in the beam path will cause artefacts. Therefore radiolucent (=low absorption) materials are of advantage for the application in CT.

For Magnetic Resonance Imaging MRI

Ferromagnetic bodies cannot be scanned at all as they would experience acceleration due to the enormous magnetic fields. Other metallic implants as e.g. eq hip implants are also potentially dangerous because of thermal injury from radiofrequency induction heating. Pacemakers and other functional devices with metallic part may fail due to exposure to these magnetic fields. Therefore also in the case of MRI, the use of polymers or composite materials is of advantage.

All the above mentioned embodiments such as the material for the pearls, the arrangement of a sensor or the constructive features as e.g. the constitution of chambers or an surrounding cylinder are freely combinable.

A sensor 18 may be disposed in the hollow space 14 for measuring pressure of the pressured air. Alternatively, the sensor 18 may be disposed on an inner side of the bag 12, and the sensor 18 may be for measuring blood pressure.

LIST OF REFERENCE NUMERALS 1 immobilizing device
2 part of a body, forearm
10 outer shell, inelastic outer shell
11 valve
12 bag
13 wall
14 air, hollow space, chamber
15 granular material; pearls; pearls made of polystyrene
16 cast
17 bar

LIST OF SYMBOLS

F Force

REFERENCES

[1] U.S. Pat. No. 5,009,318 <<Method, device and padded product for maintaining an object>>Dominique Lepinoy, FR—Dijon Publication date 23 Apr. 1991.

[2] EP 1 582 187 B1 <<Hybrid immobilisation device>>Orfit Industries, BE—2110 Wijnegen Publication 5 Oct. 2005.

[3] U.S. Pat. No. 6,882,878 B2 <<Restraining Apparatus and method for use in imaging procedures>>Berndt P. Schmit, et al., US—Salt Lake City Publication date 1 Jul. 2004.

[4] WO 2006/110028 A1 <<Immobilization device for immobilizing a lower leg, pressure device apparently suitable for use in the immobilization device, and method for manufacturing the pressure device>>Somas Groep B. V.; NL—3261 VB Oud Beijerland Publication date 19 Oct. 2006.

[5] U.S. Pat. No. 4,657,003 <<Immobilizer device>>H. Robert Wirtz, Westlake Village, Calif. Publication date 14 Apr. 1987.

The invention claimed is:

1. An immobilizing device for immobilizing a body part, the device comprising:
   an outer shell;
   a cast to position the body part;
   a bag to be placed over said cast and the body part, said bag being mounted in said outer shell;
   a granular material filling said bag; and
   said outer shell and said bag forming a hollow space therebetween for receiving pressured air to produce a force on said bag for immobilizing the body part.

2. The immobilizing device according to claim 1, wherein said outer shell includes a valve for introduction of the pressured air.

3. The immobilizing device according to claim 1, which further comprises a sensor disposed in said hollow space for measuring pressure of the pressured air.

4. The immobilizing device according to claim 1, which further comprises a sensor disposed on an inner side of said bag.

5. The immobilizing device according to claim 4, wherein said sensor is a sensor for measuring blood pressure.

6. The immobilizing device according to claim 1, wherein said granular material is pearls formed of polystyrene.

7. The immobilizing device according to claim 1, wherein said granular material fully surrounds the body part when said bag is placed over said cast and the body part.

* * * * *